(12) United States Patent
Connolly

(10) Patent No.: US 6,248,529 B1
(45) Date of Patent: Jun. 19, 2001

(54) METHOD OF CHEMICALLY ASSEMBLING NANO-SCALE DEVICES

(75) Inventor: Dennis Michael Connolly, Rochester, NY (US)

(73) Assignee: Integrated Nano-Technologies, LLC, Rochester, NY (US)

( * ) Notice: Subject to any disclaimer, the term of this patent is extended or adjusted under 35 U.S.C. 154(b) by 0 days.

(21) Appl. No.: 09/315,750

(22) Filed: May 20, 1999

Related U.S. Application Data

(60) Provisional application No. 60/086,163, filed on May 20, 1998, and provisional application No. 60/095,096, filed on Aug. 3, 1998.

(51) Int. Cl.[7] .............................. C12Q 1/68; C12P 19/34; C12N 11/00; C12N 1/12; G01N 33/543
(52) U.S. Cl. ................. 435/6; 435/6; 435/91.1; 435/91.2; 435/174; 435/183; 435/283.1; 436/418; 436/525; 536/23.1; 536/24.3; 536/24.31; 536/24.32; 536/24.33
(58) Field of Search .............................. 435/6, 91.1, 91.2, 435/174, 183, 283.1, 285.1, 285.2; 436/518, 525; 536/23.1, 24.3, 24.31, 24.32, 24.33

(56) References Cited

U.S. PATENT DOCUMENTS

| | | |
|---|---|---|
| 4,522,932 | 6/1985 | Mitchell, III . |
| 4,728,591 | 3/1988 | Clark et al. . |
| 4,802,951 | 2/1989 | Clark et al. . |
| 5,242,877 | 9/1993 | Dobson et al. . |
| 5,258,627 | 11/1993 | Turin . |
| 5,389,401 | 2/1995 | Gordon . |
| 5,536,858 | 7/1996 | Lalonde et al. . |
| 5,561,071 | 10/1996 | Hollenberg et al. . |
| 5,578,248 | 11/1996 | Hattori et al. . |
| 5,593,839 | 1/1997 | Hubbell et al. . |
| 5,632,957 | 5/1997 | Heller et al. . |
| 5,733,729 | 3/1998 | Lipshutz et al. . |
| 5,736,257 | 4/1998 | Conrad et al. . |
| 6,051,380 | * 4/2000 | Sosnowski et al. ............ 435/6 |

FOREIGN PATENT DOCUMENTS

| | | |
|---|---|---|
| WO 98/53841 | 12/1998 | (WO) . |
| WO 99/04440 | 1/1999 | (WO) . |

OTHER PUBLICATIONS

Smith et al., "Quadruplex Structure of Oxytricha Telomeric DNA Oligonucleotides," *Nature*, 356:164–168 (1992).

* cited by examiner

*Primary Examiner*—Kenneth R. Horlick
*Assistant Examiner*—Jeffrey Siew
(74) *Attorney, Agent, or Firm*—Nixon Peabody LLP

(57) ABSTRACT

The present invention provides nano-scale devices, including electronic circuits, using DNA molecules as a support structure. DNA binding proteins are used to mask regions of the DNA as a material, such as a metal is coated onto the DNA. Included in the invention are DNA based transistors, capacitors, inductors and diodes. The present invention also provides methods of making integrated circuits using DNA molecules as a support structure. Methods are also included for making DNA based transistors, capacitors, inductors and diodes.

32 Claims, 4 Drawing Sheets

METHOD OF CHEMICALLY ASSEMBLING NANO-SCALE DEVICES

The present application claims the benefit of U.S. Provisional Patent applications serial Nos. 60/086,163, filed May 20, 1998, and 60/095,096, filed Aug. 3, 1998.

BACKGROUND OF THE INVENTION

Computer chip design has improved at a rapid pace. According to Moore's law, the number of switches which can be produced on a computer chip has doubled every 18 months. Chips now can hold millions, of transistors. However, it is becoming increasingly difficult to increase the number of elements on a chip using present technologies. At the present rate, in the next few years the theoretical limit of silicon based chips will be reached. Since, the data storage and processing capabilities of microchips are determined by the number of elements which can be manufactured on a chip, new technologies are required which will allow for the development of higher performance chips.

Present chip technology is also limiting when wires need to be crossed on a chip. For the most part, the design of a computer chip is limited to two dimensions. Each time a circuit must cross another circuit, another layer must be added to the chip. This increases the cost and decreases the speed of the resulting chip.

A number of alternatives to standard silicon based complementary metal oxide semiconductor ("CMOS") devices have been proposed, including single electron transistors, quantum cellular automata, neural networks, and molecular logic devices. (Chen et al., *Appl. Phys. Lett.* 68:1954 (1996); Tougaw, et al, *J. Appl. Phys.* 75:181 (1994); Caldwell, et al., *Science* 277:93 (1997); Mead, *Proc. IEEE* 78:1629 (1990); Hopfiled, et al., *Science* 233:625 (1986); Aviram, et al., *Chem. Phys. Lett.* 29:277 (1974); and Petty et al. Eds., *Introduction to Molecular Electronics* (Edward Arnold, London, 1995)). The common goal is to produce logic devices on a nanometer scale. Such dimensions are more commonly associated with molecules than integrated circuits.

DNA molecules has recently been used as a support structure for the formation of 100 nanometer scale silver wires (Braun et al., "DNA-Templated Assembly and Electrode Attachment of a Conducting Silver Wire," *Nature* 391:775–78 (1998); PCT Application WO 99/04440, which are hereby incorporated by reference). Furthermore, the DNA molecule allows for specific targeting of the end of the DNA-wire to complimentary nucleotide sequences on a chip. The reduced size of these wires allows for a lower level of voltage to be used in a circuit, decreases operating temperatures and magnetic field strength, and faster circuits.

Integrated circuits on computer chips require numerous structures including, resistors, capacitors, and transistors. Therefore, the reduction of wiring to the 100 nanometer level may somewhat reduce the size of integrated circuits but the improvements are limited by the size of the other components.

Nucleic acid molecule directed assembly is also advantageous because it can direct the synthesis of three dimensional structures. Inductors can not be constructed on conventional chips, because they are three dimensional structures. Molecular biology provides tools for manipulating nucleic acid molecules at the molecular level. Nucleic acid molecules also provide other advantages, since nucleic acid molecules can be rapidly replicated with high fidelity using existing technologies. Furthermore, nucleic acid molecules can store information in their structure which can be used to direct the formation of complex circuits.

"DNA computers" have also been described recently in the literature in which computation occurs via chemical reactions. (Adelman, *Science* 266:1021 (1994), which is hereby incorporated by reference). This method has limited usefulness, because the nucleic acid molecules must be synthesized, reacted together, and the appropriate "result" must be isolated and sequenced. Thus, it is unclear how this technology could be used for everyday applications.

Therefore, new methods of fabricating integrated circuit components are needed, where elements of an integrated circuit can be manufactured on a nano scale. Furthermore, a need exists for taking advantage of the information coding capabilities of DNA in the formation of integrated circuits.

SUMMARY OF THE INVENTION

The present invention provides a method of masking a region of a nucleic acid molecule by binding a nucleic acid binding molecule to a binding site on the nucleic acid molecule, coating the non-protected portions of the nucleic acid molecule with a material, and removing the nucleic acid binding molecule from the nucleic acid molecule.

A method of manufacturing a nano-scale device using a nucleic acid molecule as a template is also provided by providing a nucleic acid molecule template, protecting a region or regions of the template using a nucleic acid binding molecule, coating the unprotected regions with a first material, removing the nucleic acid binding molecule, and coating the unprotected and uncoated regions of the template with a second material to form a nano-scale device.

A method of manufacturing a circuit element using a nucleic acid molecule as a template is also provided by providing a nucleic acid molecule template, protecting a region or regions of the template using a nucleic acid binding molecule, coating the unprotected regions with a first material, removing the nucleic acid binding molecule, and coating the unprotected and uncoated regions of the template with a second material to form a circuit element, where the second electrically conductive or insulating material is different from the first second electrically conductive or insulating material.

A further embodiment of the present invention is a circuit element having a nucleic acid template where two or more regions of the template are coated with different materials.

The invention also provides a resistor, a capacitor, an inducer, and a transistor each having a nucleic acid molecule template.

Yet another embodiment of the invention is a method of forming a circuit element by applying a semiconductor to a nucleic acid molecule.

DETAILED DESCRIPTION OF THE INVENTION

Figure 1:
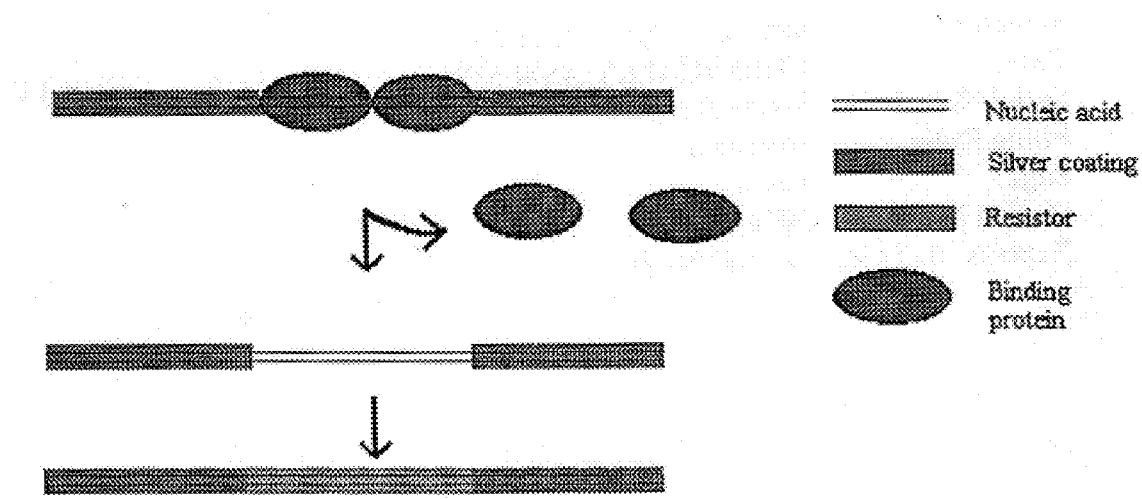
FIG. 1 shows a method for the assembly of a circuit element using masking proteins.

The present invention provides methods for manufacturing nano-scale devices, including circuit elements using a nucleic acid molecule as a template. The sequence of the nucleic acid molecule is used to direct the formation of the device. Nucleic acid molecule binding proteins or nucleic acids can be used to protect regions of the nucleic acid molecule, masking it for the later deposition of desired coating metals or other substrates.

Devices can be assembled either by forming a complete DNA template structure and then applying the coating materials in one or more steps or by assembling various subunits of the device and then assembling the subunits into a single device. The present invention is well suited for assembly of subunits by providing a method for protecting exposed DNA tags which can then direct the assembly of the subunits. Homologous tags are used to join subunits at the desired location.

In a preferred embodiment of the invention, the device consists of an electronic circuit. However, the method of the present invention can be used to direct the formation of any nano-scale structure, including mechanical and structural elements.

Circuits refers to any assembly of one or more circuit elements. The terms integrated circuit or electronic circuit are used interchangeably with circuit within this application. The methods of the present invention can be used to produce extremely small scale circuit elements which can in turn be used to produce logic circuits. Therefore, the present invention is applicable for the synthesis of relatively simple electronic circuits comprising just a few elements up to the synthesis of complicated computer circuits with millions of circuit elements.

The present invention provides for the chemical assembly of integrated circuits. A method is provided which allows the chemical synthesis of various electronic components, e.g. wires, switches, and memory elements. The method also allows for the self-ordering of the electronic components into a working computer or electronic circuit. The present invention relies on biologically directed chemical assembly, but the operation of the circuit is electronic.

The present invention provides a method of masking a region of a nucleic acid molecule by binding a nucleic acid binding molecule to a binding site on the nucleic acid molecule, coating the non-protected portions of the nucleic acid molecule with a material, and removing the nucleic acid binding molecule from the nucleic acid molecule.

A method of manufacturing a circuit element using a nucleic acid molecule as a template is also provided by providing a nucleic acid molecule template, protecting a region or regions of the template using a nucleic acid binding molecule, coating the unprotected regions with a first material, removing the nucleic acid binding molecule, and coating the unprotected and uncoated regions of the template with a second material to form a circuit element, where the second electrically conductive or insulating material is different from the first second electrically conductive or insulating material.

The method of manufacturing a circuit element may further consist of disrupting or removing the DNA template from the circuit or a portion thereof. Nucleic acid molecules have intrinsic electric properties, which may interfere with the functioning of certain circuit elements. One may take into account the electrical properties of the nucleic acid molecule in the design of the element. Where it is not possible to incorporate the intrinsic properties of the nucleic acid molecule into the circuit element, it may be preferred to disrupt or remove the nucleic acid molecule or a portion of the molecule.

In addition to applying the material to the nucleic acid molecule. A coating material may be applied over the material to prevent coating of the first material by later applied materials. Such a coating may be permanent or may be removed at a later stage in the processing of the circuit.

By carefully choosing the sequence of the nucleic acid template and the binding proteins to be used, large and complicated circuits can be assembled in solution. The self-assembling nature of the circuits would allow for the rapid and inexpensive formation of complicated circuits. Even if there is some lack of fidelity, functional circuits could be tested for and selected for further use. More complicated structures can be manufactured using combinations of nucleic acid binding compounds.

Various combinations of proteins or nucleic acids can be used to protect the nucleic acid molecule. The choice of the protecting molecule will be made based upon the size of the region to be protected and the binding affinity of the protecting molecule. After applying a metal or other substrate to the nucleic acid molecule template, some or all of the protecting proteins are removed from the nucleic acid molecule. Additional rounds of protecting the nucleic acid molecule with binding molecules and subsequent coating can be carried out to create various circuit elements.

In the present invention, preferred nucleic acid molecules include RNA and DNA. Also included within the invention are chemically modified nucleic acid molecules or nucleic acid analogs. Such RNA or DNA analogs comprise but are not limited to 2'-O-alkyl sugar modifications, methylphosphonate, phosphorothioate, phosphorodithioate, formacetal, 3'-thioformacetal, sulfone, sulfamate, and nitroxide backbone modifications, amides, and analogs wherein the base moieties have been modified. In addition, analogs of oligomers may be polymers in which the sugar moiety has been modified or replaced by another suitable moiety, resulting in polymers which include, but are not limited to, polyvinyl backbones (Pitha et al., "Preparation and Properties of Poly (I-vinylcytosine)," *Biochim Biophys Acta* 204:381–8 (1970); Pitha et al., "Poly(1-vinyluracil): The Preparation and Interactions with Adenosine Derivatives," *Biochim Biophys Acta* 204:39–48 (1970), which are hereby incorporated by reference), morpholino backbones (Summerton, et al., "Morpholino Antisense Oligomers: Design, Preparation, and Properties," *Antisense Nucleic Acid Drug Dev* 7:187–9 (1997) and peptide nucleic acid (PNA) analogs (Stein et al., "A Specificity Comparison of Four Antisense Types: Morpholino, 2'-O-methyl RNA, DNA, and Phosphorothioate DNA," *J. Antisense Nucleic Acid Drug Dev.* 7:151–7 (1997); Egholm, et al. Peptide Nucleic Acids (PNA)-Oligonucleotide Analogues with an Achiral Peptide Backbone, (1992); Faruqi et al., "Peptide nucleic acid-targeted mutagenesis of a chromosomal gene in mouse cells," *Proc. Natl. Acad. Sci. USA* 95:1398–403 (1998); Christensen, et al. "Solid-Phase Synthesis of Peptide Nucleic Acids," *J. Pept. Sci.* 1:175–83 (1995); Nielsen et al., "Peptide Nucleic Acid (PNA). A DNA Mimic with a Peptide Backbone," *Bioconjug. Chem.* 5:3–7 (1994), which are hereby incorporated by reference). In addition linkages may contain the following exemplary modifications: pendant moieties, such as, proteins (including, for example, nucleases, toxins, antibodies, signal peptides and poly-L-lysine); intercalators (e.g., acridine and psoralen), chelators (e.g., metals, radioactive metals, boron and oxidative metals), alkylators, and other modified linkages (e.g., alpha anomeric nucleic acids). Such analogs include various combinations of the above-mentioned modifications involving linkage groups and/or structural modifications of the sugar or base for the purpose of improving RNAseH-mediated destruction of the targeted RNA, binding affinity, nuclease resistance, and or target specificity.

Nucleic acid molecules can be used to form a complex support structures, including three dimensional structures (Chen et al., "Synthesis from DNA of a Molecule with the Connectivity of a Cube," *Nature* 350:631–633 (1991), which is hereby incorporated by reference). Because of the self-assembling nature of complimentary nucleic acid molecules, complex structures can be assembled in one reaction. Methods for the making and manipulation of nucleic acid molecules, including synthesis, ligation, restriction, modification, hybridization and separation can be found in *Short Protocols in Molecular Biology, A Compendium of Methods from Current Protocols in Molecular Biology*, Ausubel, F. M., et al., editors, 2nd Edition, Green Publishing Associates and John Wiley and Sons, New York (1992); Sambrook et al., *Molecular Cloning: a Laboratory Manual*, Cold Spring Harbor, N.Y., Cold Spring Harbor Laboratory, (1989), which are hereby incorporated by reference.

Directed formation of the nucleic acid support structure is carried out by sequence specific hybridization (*Short Protocols in Molecular Biology, A Compendium of Methods from Current Protocols in Molecular Biology*, Ausubel, F. M., et al., editors, 2nd Edition, Green Publishing Associates and John Wiley and Sons, New York (1992); Sambrook et al., *Molecular Cloning: a Laboratory Manual*, Cold Spring Harbor, N.Y., Cold Spring Harbor Laboratory, (1989), which are hereby incorporated by reference). A large circuit may be formed in one step or in multiple hybridization steps, where subunit portions of the support are assembled at a later stage. Hybridization conditions can be determined using formulas well known in the art (See Southern, et al., *J. Mol. Biol.*, 98:503–517 (1979), which is hereby incorporated by reference), Native nucleic acid molecules, as well as modified nucleic acids, may form triple or four stranded arrangements which can be used Bring together three or more leads (Footer, et al. "Biochemical Evidence that a D-loop is Part of a Four-Stranded PNA-DNA Bundle. Nickel-Mediated Cleavage of Duplex DNA by a Gly-Gly-His bis-PNA," *Biochemistry* 35 (33): 10673–9 (1996), which is hereby incorporated by reference).

Suitable nucleic acid molecules can be made synthetically. A preferred method for manufacturing synthetic nucleic acid molecules is the standard phosphoramidite chemistry method using either an Applied Biosystems 380B or a Milligen 7500 automated DNA synthesizer (Van Ness et al., *Nucl. Acids Res.* 19: 3345–3350 (1991); Van Ness et al, *Nucl. Acids Res.* 19: 5143–5151 (1991), which are hereby incorporated by reference).

Alternatively, portions of the structure may be assembled independently and the resulting parts assembled into the final structure, either before or after coating the nucleic acid molecules. Post-coating assembly may be facilitated by protecting the portions of the nucleic acid molecules, which will hybridize to the other parts, with nucleic acid binding proteins. These proteins may be removed prior to self-assembly of the final structure.

Once isolated or synthesized, multiple copies of the nucleic acid molecules may be prepared using PCR technology (Kawasaki, 1990, PCR Protocols: A Guide to Methods and Applications, Innis et al. eds. Academic Press, San Diego; and Wang and Mark, PCR Protocols: A Guide to Methods and Applications, Innis et al. eds. Academic Press, San Diego (1990), which is hereby incorporated by reference).

In addition to building a scaffold or support for the circuit out of nucleic acids, other materials may also be used. Nucleic acids can be attached to particles or chips to support the formation and stability of the circuit (Mirkin et al., "A DNA-Based Method for Rationally Assembling Nanoparticles into Macroscopic Materials," *Nature* 382:607–611 (1996); Fodor et al., U.S. Pat. No. 5,445,934, "Array of Oligonucleotides on a solid surface" (1995), which is hereby incorporated by reference).

After hybridization, the stability of the structure may be increased by ligation of breaks in the molecules (Stryer, *Biochemistry* $2^{nd}$ Ed., W. H. Freeman & Co., (1975), which is hereby incorporated by reference).

Restriction endonucleases can be used to break unwanted connections. For example, some fragments may be used to assist in the formation of the final structure but may not be needed in the final structure. Therefore, after formation of the structure, restriction endonucleases may be used to remove those fragments which are not desired in the final structure.

Nucleic acids produced by PCR or synthesis must be carefully produced to maintain fidelity. Fidelity may be improved by including a mismatch repair system. For example including the mut mismatch repair enzymes from *Escherichia coli*. Fidelity may also be affected by varying temperature and salt conditions. In a preferred method, high fidelity polymerases or mutant polymerases are utilized to ensure the fidelity of nucleic acid replication.

Alternatively, naturally occurring nucleic acid molecules may be selected and isolated from living organisms, including viruses, bacteria, plants and animals. Desired nucleic acids may be isolated from the organisms using methods known to those skilled in the art. For example, natural sequences may be amplified and isolated using PCR technology. Preferred naturally occurring sequences would include regions upstream of genes which consist of promoter or enhancer elements. Such regions would be rich in binding sites for nucleic acid molecule binding proteins.

The nucleic acid molecules may also be modified, to facilitate coating of the nucleic acid molecule at improved levels or with a wider variety of materials. For example, analogues of the common deoxyribo- and ribonucleosides which contain amino groups at the 2' or 3' position of the sugar can be made using established chemical techniques. (See, Imazawa et al., *J. Org. Chem.* 44:2039 (1979); Imazawa et al., *J. Org. Chem.* 43(15):3044 (1978); Verheyden et al., *J. Org. Chem.* 36(2):250 (1971); Hobbs et al., *J. Org. Chem.* 42(4):714 (1977), which are hereby incorporated by reference). In addition, oligonucleotides may be synthesized with 2'-5' or 3'-5' phosphoamide linkages (Beaucage et al., *Tetrahedron* 49(10):1925 (1992); Letsinger, *J. Org. Chem.* 35:3800 (1970); Sawai, *Chem. Left.* 805 (1984); F. Eckstein, Ed., *Oligonucleotides and Analogues: A Practical Approach* (Oxford University Press 1991), which are hereby incorporated by reference).

Amplification of a selected, or target, nucleic acid sequence may be carried out by any suitable means. (See generally Kwoh, D. and Kwoh, T.,*Am Biotechnol Lab*, 8, 14 (1990) which is hereby incorporated by reference.) Examples of suitable amplification techniques include, but are not limited to, polymerase chain reaction, ligase chain reaction (see Barany, *Proc Natl Acad Sci USA* 88, 189 (1991), which is hereby incorporated by reference), strand displacement amplification (see generally Walker, G. et al., *Nucleic Acids Res.* 20, 1691 (1992); Walker. G. et al., *Proc Natl Acad Sci USA* 89, 392 (1992), which are hereby incorporated by reference), transcription-based amplification (see Kwoh, D. et al., *Proc Natl Acad Sci USA*, 86, 1173 (1989), which is hereby incorporated by reference), self-sustained sequence replication (or "3SR") (see Guatelli, J. et al., *Proc Natl Acad Sci USA*, 87, 1874 (1990), which is hereby incorporated by reference), the Qb replicase system (see Lizardi, P. et al., *Biotechnology*, 6, 1197 (1988), which is hereby incorporated by reference), nucleic acid sequence-based amplification (or "NASBA") (see Lewis, R., *Genetic Engineering News*, 12(9), 1 (1992), which is hereby incorporated by reference), the repair chain reaction (or "RCR") (see Lewis, R., *Genetic Engineering News*, 12(9), 1 (1992), which is hereby incorporated by reference), and boomerang DNA amplification (or "BDA") (see Lewis, R., *Genetic Engineering News*, 12(9), 1 (1992), which is hereby incorporated by reference). Polymerase chain reaction is currently preferred.

In general, DNA amplification techniques such as the foregoing involve the use of a probe, a pair of probes, or two pairs of probes which specifically bind to the nucleic acid molecule of interest, but do not bind to other nucleic acid molecules which are not desired, under the same hybridization conditions, and which serve as the primer or primers for the amplification of the nucleic acid molecule of interest or a portion thereof in the amplification reaction.

The sequence of the templates can be verified by sequencing the molecules by either chemical (Maxam et al., *Proc. Nat'l Acad. Sci. USA*, 74:560 (1977), which is hereby incorporated by reference) or enzymatic methods (Sanger, et al., *Proc. Nat'l Acad. Sci. USA*, 74:5463 (1977), which is hereby incorporated by reference).

The nucleic acid molecule itself may have some conductive properties of its own. These properties may be modified to reduce any detrimental effects on the function of the electronic circuit (Meade, et al, U.S. Pat. No. 5,770,369, "Nucleic Acid Mediated Electron Transfer" (1998), which is hereby incorporated by reference). Modification of the electrical properties of the nucleic acid molecule may be made by intercalating compounds between the bases of the nucleic acid molecule, modifying the sugar-phosphate backbone, or by cleaving the nucleic acid molecule after the circuit elements are formed. Cleavage of the nucleic acid molecule may be accomplished by irradiation, chemical treatment, or enzymatic degradation. Irradiation using gamma-radiation is preferred because radiation may penetrate materials coating the nucleic acid molecule.

In another embodiment of the invention, one strand of a double stranded nucleic acid molecule is modified to decrease or inhibit coating of that strand. The coated nucleic acid molecule would then be coated on only one side, allowing for the chemical or enzymatic removal of the nucleic acid template after the formation of the circuit elements.

Masking of nucleic acids from coating can be carried out with nucleic acid binding proteins, nucleic acid molecules, antibodies, or other compounds which can interact stably with the nucleic acid molecule and block access to the nucleic acid molecule. In a preferred embodiment of the invention, nucleic acid binding proteins are used to protect the nucleic acid molecule from coating.

Nucleic acid binding molecules may be sequence preferential or sequence specific. Sequence-preferential binding refers to nucleic acid binding molecules that generally bind nucleic acid molecules but that show preference for binding to some sequences over others. Sequence-preferential binding is typified by small molecules, e.g., distamycin. Many nucleic acid binding molecules are known and their interactions with the nucleic acid molecules have been studied. (See e.g., Boulikas, "A Compilation and Classification of DNA Binding Sites for Protein Transcription Factors from Vertebrates," *Crit. Rev. Eukayot. Gene Expr.* 4:117–321 (1994), which is hereby incorporated by reference). Such nucleic acid molecules include transcriptional and translational activators, repair enzymes, histones, ligases, restriction nucleases, etc.

The available nucleic acid binding proteins number in the hundreds. In addition, modified or mutant binding proteins increase the number of available proteins for use in the present invention. Selection of the appropriate nucleic acid binding protein will be based upon a number of factors. Among the more significant factors, the size of the region protected by the binding protein will determine the protein to be used. The electrical function of an element will often be dependent upon the length of the element. Thus the size of the protected region is important in creating an element with the desired properties. Some proteins may also form multimers more readily for protecting larger regions of the nucleic acid molecule. Another factor to be considered when choosing a binding protein is the affinity of the protein for its target sequence. A higher affinity may be useful for decreasing the frequency of malformed elements. On the other hand, the affinity should be at a level where the binding protein can be effectively removed when needed. Since several different proteins will be needed in the production of more complex circuits, the compatibility of the various proteins will also be a factor. Proteins are desired which can be removed effectively, without affecting the protection by the other binding proteins being used.

Ligases can be utilized to increase the stability of the DNA template after the fragments have been allowed to hybridize. Ligation will make the structure more resistant to denaturation by heat or salt in further steps.

In addition, endo or exo-nucleases may be used to remove portions of the support structure when they are no longer needed. Nucleic acid molecules may be used to hold parts of the structure in place during coating and then removed later.

Preferred nucleic acid binding molecules are regulatory molecules. In particular, the lac and tet repressor proteins have been well studied. The lactose repressor protein may be prepared as described in the literature: Rosenberg, J. M. et al., *Nucleic Acid Res.* 4(3):567 (1977); Matthews, K. S., *J. Biol. Chem.* 253(12):4279 (1978); O'Gorman, R. B. et al., *J. Biol. Chem.* 255(21):10100 (1980); Levens, D. and P. M. Howley, Mol. Cell. Biol. 5(9):2307 (1985), which are hereby incorporated by reference. The presence, activity and degree of purity of the lactose repressor protein prepared using the above referenced methods can be determined using procedures described in the literature. (Bourgeois, S. and A. D. Riggs, *Biochem. Biophys. Res. Comm.* 38(2):348 (1970); Barkley, M. D. and S. Bourgeois in *The Operon*, Cold Spring Harbor, N.Y. pp. 177–220 (1978); and Bourgeois, S. in *Methods in Enzymology* Vol. 21, pp. 491–500 (1971), which are hereby incorporated by reference.)

The tetracycline (tet) repressor protein may be prepared as described in the literature: Hillen et al., *J. Mol. Biol.* 257(11):6605 (1982); Oehmichen et al., *EMBO J.* 3(3):539 (1984), which are hereby incorporated by reference. The tet repressor protein may be assayed and characterized as described by: Altschemied et al., *J. Mol. Biol.* 187:341 (1986); Hillen et al., *J. Mol. Biol.* 172:185 (1984); Hillen et al., *J. Mol. Biol.* 169:707 (1983), which are hereby incorporated by reference.

Also preferred are restriction endonucleases. Proteins such as restriction nucleases have well known binding sequences. However, the nuclease activity may not be desired. Appropriate buffer conditions may be used to facilitate binding to the nucleic acid but prevent cleavage of the template molecule. Similarly, other proteins may require cofactors for activity and thus undesired activities may be regulated by omitting necessary cofactors. (Chiang et al., "Effects of Minor Groove Binding Drugs on the Interaction of TATA Box Binding Proteins and TFIIA with DNA," *Biochemistry* 33:7033–40 (1994); Wu et al., "Physical and Functional Sensitivity if Zinc Finger Transcription Factors to Redox Change," *Mol. Cell. Biol.* 16:1035–46 (1996); Aranyi et al., "Gluccocorticoid Receptor is Activated by Heparin and Deactivated by Plasmin," *Acta Biochem. Biophy. Acad. Sci. Hung.* 20:129–33 (1985); Ralston et al., "Metalloregulatory Proteins and molecular Mechanisms of Heavy Metal Signal Transduction," *Adv. Inorg. Biochem.* 8:1–31 (1990); Pratt, "Transformation of Gluccocorticoid and Progesterone Receptors to the DNA-Binding State," *J. Cell Biochem.* 35:51–68 (1987), which are hereby incorporated by reference). Alternatively, mutant forms of restriction endonucleases can be utilized which lack nuclease activity but maintain the sequence specific binding activity.

Fragments of nucleic acid binding proteins may also be used if they contain the functional nucleic acid binding domain. These fragments may have smaller footprints and therefore may be useful in varying the size of the protected region. Methods for identifying and isolating function nucleic acid binding fragments are known in the art (Sukhatme et al., U.S. Pat. No. 5,773,583, "Methods and Materials Relating to the Functional Domains of DNA Binding Proteins," (1998), which is hereby incorporated by reference).

Hybrid proteins can also be utilized to prepare nucleic acid-binding proteins of interest. Such hybrid proteins can be isolated by affinity or immunoaffinity columns. Further, DNA-binding proteins can be isolated by affinity chromatography based on their ability to interact with their cognate DNA binding site. Alternatively, other expression systems in bacteria, yeast, insect cells or mammalian cells can be used to express adequate levels of a nucleic acid-binding protein for use in this assay.

Mutant binding proteins also may be used. Mutations in binding proteins may result in changes in sequence specificity or affinity.

Any protein that binds to a specific recognition sequence may be useful in the present invention. One constraining factor is the effect of the immediately adjacent sequences (the test sequences) on the affinity of the protein for its recognition sequence. Nucleic acid molecule:protein interactions in which there is little or no effect of the test sequences on the affinity of the protein for its cognate site are preferable for use in the described assay; however, nucleic acid molecule:protein interactions that exhibit (test sequence-dependent) differential binding may still be useful if algorithms are applied to the analysis of data that compensate for the differential affinity. In general, the effect of flanking sequence composition on the binding of the protein is likely to be correlated to the length of the recognition sequence for the DNA-binding protein. Generally, the kinetics of binding for proteins with shorter recognition sequences are more likely to suffer from flanking sequence effects, while the kinetics of binding for proteins with longer recognition sequences are more likely to not be affected by flanking sequence composition.

The region, which is protected by a single nucleic acid binding protein, may be limited. However, multiple nucleic acid molecule binding proteins can be used to protect larger regions of the nucleic acid molecule. Indeed, some nucleic acid binding proteins, have protein-protein interactions, which facilitate the protection of large regions of nucleic acid molecules. A mixture of different binding domains can be used to set the exact length to be protected.

The concentration of the nucleic acid binding proteins is important. As one nucleic acid:protein complex dissociates, the released nucleic acid rapidly reforms a complex with another protein in solution. Since the protein is in excess to the nucleic acid, dissociations of one complex always result in the rapid reassociation of the nucleic acid into another nucleic acid:protein complex. At equilibrium, very few nucleic acid molecules will be unbound. If the unbound nucleic acid is the component of the system that is measured, the minimum background of the assay is the amount of unbound nucleic acid observed during any given measurable time period.

Removing the masking proteins from the nucleic acid molecule can be done using methods known to those skilled in the art for removing binding proteins from nucleic acids.

Some nucleic acid binding proteins, especially transcriptional and translational activators or repressors depend upon cofactors for their ability to bind to or release from a nucleic acid molecule. Thus, by adding or removing co-factors from the solution. The binding of masking proteins could be carefully regulated.

Proteins are also subject to denaturation by chemicals which do not effect the nucleic acids. For example, phenol and chloroform can be used to strip proteins from nucleic molecules without affecting the nucleic acid molecule itself.

In another method would be to increase the salt concentration of the solution surrounding the circuit. By altering the salt concentration proteins could be stripped off the nucleic acids. Moreover, by using proteins with binding coefficients having different sensitivities to salt, some proteins could be removed from the nucleic acid template while leaving other proteins still bound and thus still masking those sections of the nucleic acid molecule.

Binding proteins could be removed by the addition of a high concentration of a competitor molecule. Such a molecule would contain a binding site for the particular protein to be removed. Affinity of the binding site may be higher than that used in the template molecule or merely by increasing the concentration of the competitor molecule, the protein may be selectively removed from the template. The competitor molecule may be used in various forms, for example in solution, on a solid support, or attached to paramagnetic beads. The solid support or paramagnetic beads allows for the easy removal of much of the competitor DNA to allow the competitor DNA to be used in multiple reactions. Alternatively, when complete removal of competitor DNA is desired, nucleases can be used to digest the free DNA.

Proteins could also be removed from the nucleic acid molecule by altering the temperature of the solution. Proteins lose their ability to maintain their structure and activity at higher temperatures. Thus by increasing temperature, proteins can be inactivated. However, if temperature is used to remove proteins, care must be taken to design nucleic acid molecules so that the nucleic acid template will not denature. Again differential release of proteins is possible using changes in temperature. Thermostable enzymes can be isolated from certain organisms. For instance, thermophilic bacteria produce proteins, which maintain their activity at temperatures above 80° C. Thus using a mixture of proteins allows for the release of some proteins while maintaining the masking of other sites.

Temperature does denature nucleic acid sequences (Casey et al., *Nucl. Acids Res.* 4:1539 (1977), which is hereby incorporated by reference). Therefore, when using temperature to remove proteins from the nucleic acid molecule, the melting temperature of the nucleic acid molecule should be taken into account. The stability of the template may be improved by ligating molecules nucleic acid molecules together.

Of course the removal of proteins can be facilitated by a combination of various methods, such as altering both salt concentrations and temperature (See e.g., Koblan et al., *Biochem.* 30:7817–21 (1991), which is hereby incorporated by reference).

The negatively charged backbone of a nucleic acid molecule can be used to attract and attach materials necessary to form circuit elements. Metals, doped metals, and other materials can be specifically bound to exposed regions of a DNA molecule.

For example, DNA can be used to form metal or metal composite wires (Braun et al., *Nature* 391:775 (1998), which is hereby incorporated by reference). Braun demonstrated that silver could be deposited along a DNA molecule. A three-step process is used. First, silver is selectively localized to the DNA molecule through a $Ag^+/Na^+$ ion-exchange (Barton, in *Bioinorganic Chemistry* (eds Bertini, et al.) ch. 8 (University Science Books, Mill Valley, 1994, which is hereby incorporated by reference) and complexes are formed between the silver and the DNA bases (Spiro (ed.) *Nucleic Acid-Metal Ion Interactions* (Wiley Interscience, New York 1980; Marzeilli, et al., *J. Am. Chem. Soc.* 99:2797 (1977); Eichorn (ed.) *Inorganic Biochemistry,* Vol. 2, ch 33–34 (Elsevier, Amsterdam, 1973), which are hereby incorporated by reference). The ion-exchange process may be monitored by following the quenching of the fluorescence signal of the labeled DNA.. The silver ion-exchanged DNA is then reduced to form aggregates with bound to the DNA skeleton. The silver aggregates are further developed using standard procedures, such as those used in photographic chemistry (Holgate, et al., *J. Histochem. Cytochem.* 31:938 (1983); Birell, et al., *J. Histochem. Cytochem.* 34:339 (1986), which are hereby incorporated by reference).

Chemical deposition of conductors, semi-conductors, or other materials can be carried out using chemical techniques known in the art. As an example, photographic dyes can be used with silver in known photochemical reactions. (James, *The Theory of the Photographic Process,* $4^{th}$ ed. (Macmillan Publishing, New York 1977), which is hereby incorporated by reference) Photographic dyes, like other solid organic compounds containing π-electron chromophores, such as aromatic hydrocarbons, are electronic semiconductors and photoconductors (James, *The Theory of the Photographic Process,* $4^{th}$ ed. (Macmillan Publishing, New York 1977); Kallman et al. eds., *Symposium on Electric Conductivity of Organic Solids* (Wiley-Interscience 1961); Meier, *Die Photochemie der Organischen Farbstoffe* (Springer, Berlin 1963); Gutman et al., *Organic Semiconductors* (Wiley, New York 1967); Meier, *Spectral Sensitization* (Focal Press, London and New York 1968), which are hereby incorporated by reference).

Examples of suitable dyes which can be used as semi-conductors have been reviewed in Hamer, *The Chemistry of Heterocyclic Compounds,* Vol. 18, The Cyanine Dyes and Related Compounds, Weissberger, ed., Interscience, New York, 1964; Mees et al., eds. *The Theory of the Photographic Process* $4^{th}$ *Ed.* (Macmillan, New York 1977); Ficken, *The Chemistry of Heterocyclic Compounds,* Vol. 4, Venkataraman, ed. (Academic Press, New York 1971); and Sturmer, *The Chemistry of Heterocyclic Compounds,* Vol. 30, Weissberger et al., ed. (John Wiley, New York 1977), which are hereby incorporated by reference). Preferred dyes include cyanine and merocyanine dyes. Methods of synthesis for these compounds are well known in the art. Brooker et al., *J. Am. Chem. Soc.* 73:5326 (1951); Dimroth, et al., *Justus Liebigs Ann. Chem.* 373 (1975); Brooker et al., *J. Franklin Inst.* 219:255 (1935); Brooker et al., *J. Am. Chem. Soc.* 57:2480 (1935); Malhotra et al., *J. Chem. Soc.* 3812 (1960), which are hereby incorporated by reference). Sensitizing dyes adsorb to silver halides (Herz, *The Theory of the Photographic Process* $4^{th}$ *Ed.* Chap. 9, (Macmillan, New York 1977), which is hereby incorporated by reference). Thus dyes may be applied to the nucleic acid molecule support to produce semiconductor regions.

Metals or other materials once deposited may be doped through a variety of techniques. In one embodiment, the doping material is mixed with the metal or other material in solution to form a doped compound on the nucleic acid substrate. In another embodiment, one or materials are applied to the nucleic acid substrate and then the substrate is removed from solution and the material-substrate complex is exposed to doping agents in a gaseous state. Additional materials may then be applied to the nucleic acid substrate in additional steps.

Other positively charged ions could be deposited along a nucleic acid molecule in a similar manner. The use of a nucleic acid molecule as a template is not limited to silver, other metals can be substituted. Moreover, the invention is not limited to metals. Burroughes et al. *Nature* 347, 539 (1990), which is hereby incorporated by reference, discloses that DNA can be used as a template to fabricate a poly-(p-phenylene vinylene) ("PPV") filament by attaching a positively charged pre-PPV polymer to the stretched DNA and treating it to form a photoluminescent PPV wire.

To expand the range of materials which may be used to create circuit elements, positively charged groups may be complexed with other materials which would not normally interact with the nucleic acid molecule. The positively charged group can interact with the negatively charged nucleic acid molecule. Alternatively, desired materials may be complexed with compounds which will intercalate with the stacked base-pairs in the nucleic acid molecule. In a preferred embodiment, the intercalating agent is ethidium bromide. Intercalating molecules may also be used to alter the inherent conductivity or resistivity of the nucleic acid molecule (Meade, U.S. Pat. No. 5,770,369 (1998), which is hereby incorporated by reference).

In another embodiment, a polymer composition effective to bind, in a sequence-specific manner to a target sequence of a duplex polynucleotide, at least two different-oriented Watson/Crick base-pairs at selected positions in the target sequence may be used to target materials to the nucleic acid molecules. The polymer composition includes an uncharged backbone with 5- or 6-member cyclic backbone structures and selected bases attached to the backbone structures effective to hydrogen bond specifically with different oriented base-pairs in the target sequence (Summerton, et al., U.S. Pat. No. 5,405,938 (1995), which is hereby incorporated by reference).

In addition, during development, mixtures of metals may be used to deposit an alloy or doped material. Doping materials may be applied in a liquid state during development. The conductivity of the material may also be altered by heat treatment. Accordingly, the physical properties of the coating materials may be altered to produce desired electrical characteristics.

Once a material is deposited on the nucleic acid molecule, the nucleic acid molecule can be disrupted and/or removed by using treatments which will specifically disrupt the nucleic acid molecule but not affect the circuit elements. Nucleic acid molecules can be disrupted, or possibly removed, by treating the circuit with nucleases, ionizing radiation, oxidizing compounds. In a preferred embodiment of the invention, nucleic acid molecules are disrupted by ionizing radiation.

As discussed above, the nucleic acid molecule may be modified prior to the depositing of the coating material. Such modifications may also affect the electrical properties of the resulting material.

Portions of the nucleic acid molecule scaffolding may be used to hold the scaffolding in a particular arrangement. After metals or other materials are applied which will stabilize the structure, those segments of the nucleic acid molecules not needed in the circuit may be removed. Restriction endonucleases can be utilized to cut exposed nucleic acid molecules in a sequence dependent manner (*Short Protocols in Molecular Biology, A Compendium of Methods from Current Protocols in Molecular Biology*, Ausubel, F. M., et al., editors, 2nd Edition, Green Publishing Associates and John Wiley and Sons, New York (1992); Sambrook et al., *Molecular Cloning: a Laboratory Manual*, Cold Spring Harbor, N.Y., Cold Spring Harbor Laboratory, (1989), which are hereby incorporated by reference). Double- and single stranded nucleases may be used to digest away undesired portions of the nucleic acid molecules which are not protested by metal, other materials, or binding proteins.

Conditions may be adjusted to give a high level of fidelity in the self-assembly of a computer circuit. However, some error may occur. To overcome the occurrence of errors one may test the circuits produced using presently available techniques to identify those circuits which are correctly formed.

In addition, circuits may be designed so that the programming can identify errors and compensate for malformed elements. For example, parallel circuit systems can be designed which allow for a wide range of computational architectures. (See e.g., Bruck et al., U.S. Pat. No. 5,280,607, "Method and Apparatus for Tolerating Faults in Mesh Architectures" (1991), which is hereby incorporated by reference). Defect tolerant architectures can be created by incorporating a high communication bandwidth. The high bandwidth enables the software to route around defects (Heath et al., "A Defect-Tolerant Computer Architecture: Opportunities for Nanotechnology," *Science* 280:1716 (1998); Eaton et al., U.S. Pat. No. 4,939,694, "Defect Tolerant Self-Testing Self-Repairing Memory System" (1990), which are hereby incorporated by reference). Configurable computing systems are reviewed in Villasenor et al., *Scientific American* 276:68 (1997), which is hereby incorporated by reference.

The circuit elements of the present invention may be combined with traditional chip technology. Nucleic acid molecules can be readily attached to wafers thus directing the attachment of nucleic acid molecule based circuit elements. (Fodor et al., U.S. Pat. No. 5,445,934, "Array of Oligonucleotides on a solid surface" (1995), which is hereby incorporated by reference). Such wafers may even be used as a substrate in the formation of nucleic acid based circuits. Alternatively, the circuits may be formed and then connected to nucleic acid molecules on a wafer to integrate the nucleic acid based circuits into conventional systems.

Once the circuit is produced, it may be encapsulated in a non-conductive material to protect the circuit from damage. Preferred encapsulating agents would be plastics or glass-like materials.

The method of the present invention can be used to manufacture integrated circuits and the elements which make up integrated circuits, including, transistors, resistors, capacitors, inducers, and diodes. The circuit elements can be arranged to create logic circuits and other electronic circuits (Marston, *Digital Logic IC Pocketbook* (Reed Elsevier Pub., Boston 1996), which is hereby incorporated by reference).

The present invention can be used to build integrated circuits or to attach circuit elements to circuits made by existing technologies. In particular the invention is useful for making elements in three dimensions, something which is costly or sometimes impossible to do with conventional chip technologies. The invention may also be used to make nano-scale containers for drugs or other materials. The composition of the shell could be varied to control the release of the material from the container. The invention could also be made to construct nano-scale mechanical or structural components for various devices, rather than machining such small devices. The present invention allows for a rapid and inexpensive method for making

EXAMPLES

Example 1—A Resistor

In one embodiment of the present invention, the method is used to create a resistor FIG. 1 depicts the synthesis of a resistor element. On or more binding molecules are incubated in solution with a DNA scaffolding protein having the binding site for the binding molecule. After the binding molecule binds to the site, silver is applied to the unprotected regions of the DNA scaffolding molecule. The silver is only laid down on regions where the negatively charged DNA backbone is accessible. This step creates a silver wires leading up to both sides of the protected region. The binding molecule is then removed from the region and a different metal, doped metal or other conductive material is laid down over the protected region. The other metal, doped metal, or other conductive material has a different resistance. The strength of the resistor can be varied by varying the size of the region protected by the binding molecules.

Example 2—A Diode

Diodes consist of a p and an n type semiconductor. Since current can only flow from the p to n region, diodes limit the flow of current in one direction. Diodes are useful for the conversion of AC current to DC current.

Figure 2:
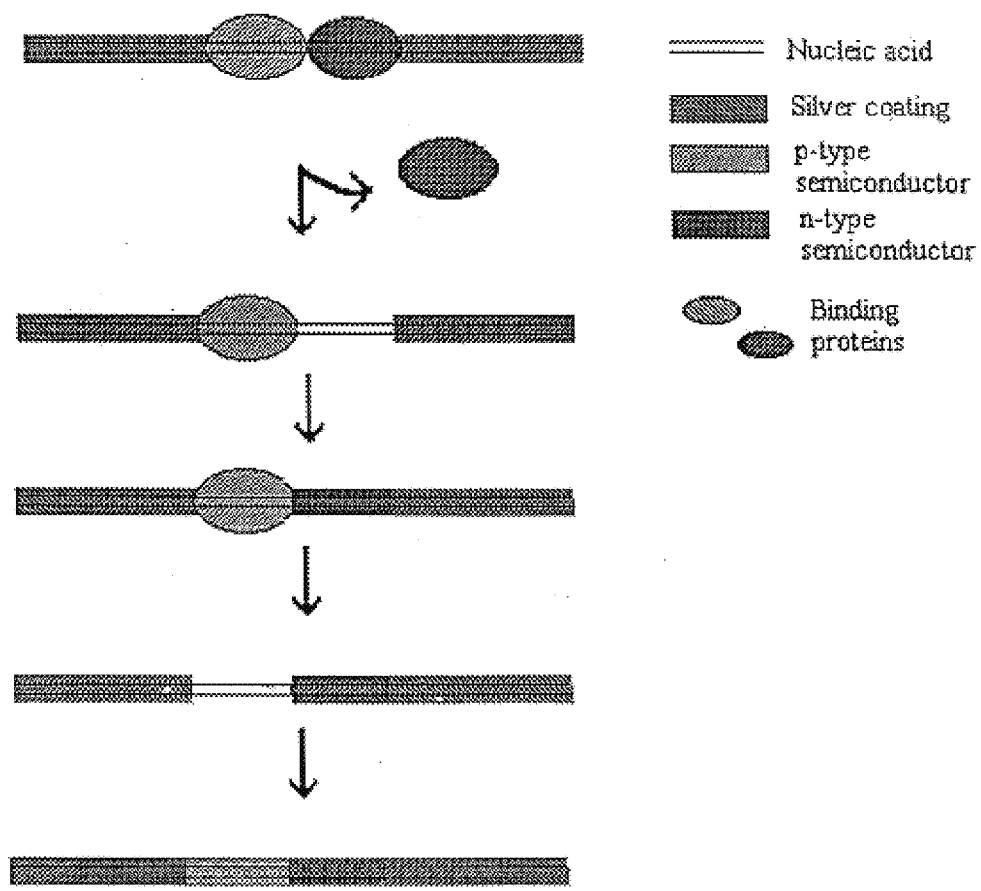
FIG. 2 shows how the method of the present invention can be used to produce a nanometer scale diode.

Diodes can be readily assembled using the present invention. FIG. 2 summarizes the synthesis of a diode. The process is similar that used to make a resistor, except that two different binding proteins can be used to protect contiguous sites. A wire is laid down over the remainder of the nucleic acid molecule. If necessary, a protective coating is applied to the wire. One of the nucleic acid binding proteins is removed from the nucleic acid molecule. A competing nucleic acid molecule with the binding site for the first binding protein may be used in a high concentration to compete off the first binding protein with little effect on the second binding protein. A p or n semiconductor is then applied to the exposed portion of the nucleic acid molecule. Again, a protective coating may be applied to the applied material. The second nucleic acid binding molecule is then removed and the n or p semiconductor, opposite that which was previously applied, is applied to the newly exposed portion of the nucleic acid molecule.

Furthermore, diodes and transistors may be assembled concurrently if the same materials are used for the p and n semiconductors for both elements.

Example 3—A Transistor

Figure 3:
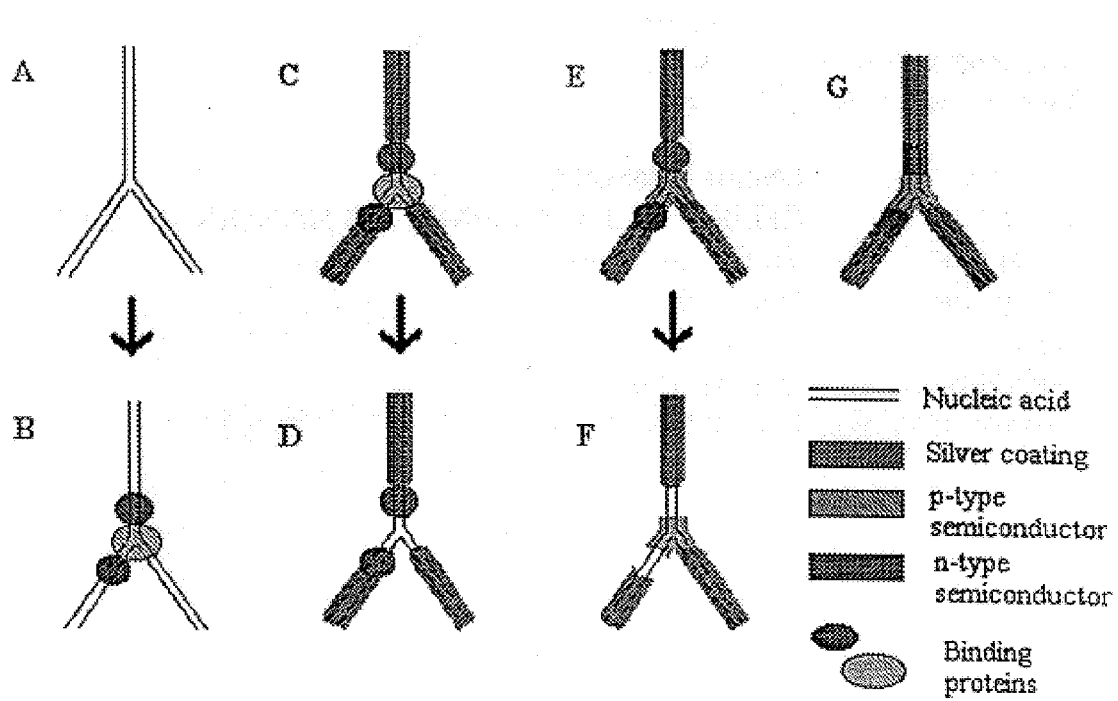
FIG. 3 shows how the method of the present invention can be used to produce a nanometer scale transistor.
Figure 4:
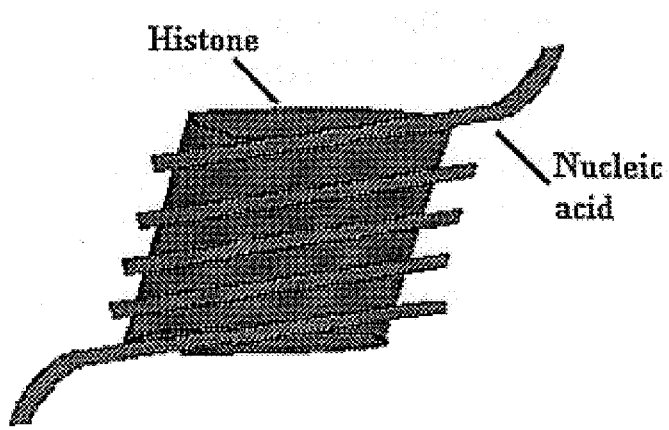
FIG. 4 shows an inducer produced by the present invention. The wire is developed around histone-like proteins which hold the nucleic acid template in a coiled configuration.

In order to make the necessary template, two nucleic acid molecules are selected where the first nucleic acid molecule can hybridize to a central portion of the second nucleic acid molecule. FIG. 3 summarizes one method for the synthesis of a transistor using a nucleic acid molecule substrate. Nucleic acid binding proteins are selected which can bind the central region. Proteins which bind specifically to X and Y nucleic acid structures are known in the art (See Elborough, et al., "Specific Binding or Cruciform DNA Structures by a Protein from Human Extracts," *Nucl. Acids Res.* 16:3603–16 (1988); Chan et al., "Recognition and Manipulation of Branched DNA by the RusA Holliday Junction Resolvase of *Escherichia coli,*" *Nucl. Acids Res.* 26:1560–66 (1998); which are hereby incorporated by reference). A second binding protein is used to protect two branches of the nucleic acid molecule adjacent to the junction binding protein. Silver wiring is deposited and the protecting molecule is removed. The junction binding protein is selectively removed from the nucleic acid molecule. This exposes a region in the middle of the previously protected region and is bound to the nucleic acid template (FIG. 3D). Either a p or n type material is deposited onto the unprotected and exposed portions of the DNA molecule (FIG. 3E). The other protecting molecules are then removed (FIG. 3F) and the exposed region is then filled in with an n or p type material to complete the transistor (FIG. 3G).

Example 4—An Inducer

Inducers produce a magnetic field which can induce a current in a nearby part of the circuit. Inducers are used as transformers to change voltage in a circuit. Inducers are also important in the formation of radio receivers. Inducers are usually formed of a coil of a conductive material. Current moving around the coil produces a magnetic field. However, a coil structure, since it is three dimensional, cannot be produced on traditional semiconductor chips.

Inducers can be produced using the present invention. One method for producing inducers relies on the use of histone-like proteins. Histone-like proteins are DNA binding proteins which are involved in the formation of nucleosomes (Wolffe, "Histone H1," *Int. J. Biochem. Cell Biol.* 29:1463–66 (1997); Zhang et al., "Characteristics of a Chlamydia psittaci DNA binding Protein (EUO) Synthesized During the Early and Middle Phases of the Developmental Cycle," *Infect. Immun.* 66:1167–73 (1998); Dutnall, et al., "Twists and Turns of the Nucleosome: Tails Without Ends," *Structure* 5:1255–59 (1997); Wintjens et al., "Structural Classification of HTH DNA Binding Domains and Protein-DNA Interaction Modes," *J. Mol. Biol.* 262:294–313 (1996); Staynov, et al., "Footprinting of Linker Histones H5 and H1 on the Nucleosome," *EMBO J.* 7:3685–91 (1988); which are hereby incorporated by reference). The DNA molecule wraps around the histone protein forming a compact coil. To produce an inducer, a nucleic acid molecule is wrapped around one or more histone proteins. After the nucleic acid molecule is formed into a coil, a metal or other conductive material is applied to the DNA, as discussed above.

After the nucleic acid molecule wraps around the histone protein, a conductive material is applied to the nucleic acid molecule. The histone protein may be removed later by chemical digestion.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of masking a region of a nucleic acid molecule comprising:

binding a nucleic acid binding molecule to a binding site on the nucleic acid molecule, coating unprotected regions of the nucleic acid molecule with a material, and removing the nucleic acid binding molecule from the nucleic acid molecule.

2. The method according to claim 1, wherein the nucleic acid molecule is DNA.

3. The method according to claim 1, wherein the nucleic acid molecule is RNA.

4. The method according to claim 1, wherein the nucleic acid binding molecule is selected from the group consisting of transcriptional and translational activators, repair enzymes, histones, ligases, and restriction nucleases.

5. The method according to claim 1, wherein more than one type of nucleic acid binding molecule is bound to the nucleic acid molecule.

6. A method of manufacturing a circuit element using a nucleic acid molecule as a template, comprising:

providing a nucleic acid molecule template, protecting a region or regions of the template using a nucleic acid binding molecule, coating unprotected regions of the nucleic acid molecule with a first material, removing the nucleic acid binding molecule, and coating unprotected and uncoated regions of the nucleic acid molecule with a second material to form a circuit element, where the second material is different from the first material.

7. The method according to claim 6, wherein the nucleic acid molecule is DNA.

8. The method according to claim 6, wherein the nucleic acid molecule is RNA.

9. The method according to claim 6, wherein the nucleic acid binding molecule is selected from the group consisting of transcriptional and translational activators, repair enzymes, histones, ligases, and restriction nucleases.

10. The method according to claim 6, wherein the first material is a conductive or insulating material.

11. The method according to claim 10, wherein said conductive or insulating material is a metal.

12. The method according to claim 11, wherein said metal is silver or gold.

13. The method according to claim 6, wherein the first material is a doped electrically conductive material.

14. The method according to claim 6, wherein the second material is a conductive or insulating material.

15. The method according to claim 6, wherein said removing the nucleic acid binding molecule is carried out by increasing salt concentration.

16. The method according to claim 6, wherein said removing the nucleic acid binding molecule is carried out by increasing temperature.

17. The method according to claim 6, wherein said removing the nucleic acid binding molecule is carried out by adding or removing a cofactor which decreases the affinity of the nucleic acid binding molecule for the binding site on the nucleic acid molecule.

18. The method according to claim 6, wherein said removing the nucleic acid binding molecule is carried out by adding a competitor nucleic acid binding site.

19. The method according to claim 6, wherein the circuit element is a resistor.

20. The method according to claim 6, wherein the circuit element is a transistor.

21. The method according to claim 6, wherein the circuit element is a capacitor.

22. The method according to claim 6, further comprising:
   disrupting or removing the DNA template or a section thereof from the circuit element.

23. The method according to claim 22, wherein said disrupting or removing is carried out using ionizing radiation.

24. The method according to claim 22, wherein said disrupting or removing is carried out using an oxidizing agent.

25. The method according to claim 22, wherein said disrupting or removing is carried out using a nuclease.

26. The method according to claim 6, wherein said providing a nucleic acid molecule template further comprises:

synthesizing oligonucleotide components, and annealing the oligonucleotide components.

27. The method according to claim 26, wherein the synthesizing oligonucleotide components is carried out by PCR amplification of a template.

28. The method according to claim 26, wherein the synthesizing of oligonucleotide components is carried out by chemical synthesis of the oligonucleotide.

29. A method of manufacturing nano-scale devices using a nucleic acid molecule as a template, comprising:

providing a nucleic acid molecule template, protecting a region or regions of the template using a nucleic acid binding molecule, coating unprotected regions of the nucleic acid molecule with a first material, removing the nucleic acid binding molecule, and coating unprotected and uncoated regions of the nucleic acid molecule with a second material.

30. The method according to claim 29, wherein the nucleic acid molecule is DNA.

31. The method according to claim 29, wherein the nucleic acid molecule is RNA.

32. The method according to claim 29, wherein the nucleic acid binding molecule is selected from the group consisting of transcriptional and translational activators, repair enzymes, histones, ligases, and restriction nucleases.

* * * * *